United States Patent [19]

Vanmaele

[11] Patent Number: 4,912,028

[45] Date of Patent: Mar. 27, 1990

[54] INTRAMOLECULAR NUCLEOPHILIC DISPLACEMENT COMPOUND AND USE IN PHOTOGRAPHY

[75] Inventor: Luc J. Vanmaele, Lochristi, Belgium

[73] Assignee: AGFA-GEVAERT, N.V., Mortsel, Belgium

[21] Appl. No.: 201,445

[22] Filed: Jun. 2, 1988

[30] Foreign Application Priority Data

Jun. 5, 1987 [EP] European Pat. Off. ........ 87201058.2

[51] Int. Cl.$^4$ .......................... G03C 1/02; G03C 1/06; G03C 7/26

[52] U.S. Cl. ..................................... 430/564; 430/566; 430/598; 430/601; 430/955; 430/957; 430/958; 430/959

[58] Field of Search ............... 430/564, 566, 598, 601, 430/955, 957, 958, 959

[56] References Cited

U.S. PATENT DOCUMENTS

| | | | |
|---|---|---|---|
| 4,371,604 | 2/1983 | Van de Sande et al. | 430/955 |
| 4,537,853 | 8/1985 | Van de Sande et al. | 430/955 |
| 4,559,290 | 12/1985 | Sawada et al. | 430/223 |
| 4,639,408 | 1/1987 | Kitaguchi et al. | 430/223 |
| 4,668,615 | 5/1987 | Kawata et al. | 430/955 |
| 4,731,321 | 3/1988 | Sato et al. | 430/955 |
| 4,734,353 | 3/1988 | Ono et al. | 430/959 |

*Primary Examiner*—Paul R. Michl
*Assistant Examiner*—Patrick A. Doody
*Attorney, Agent, or Firm*—A. W. Breiner

[57] ABSTRACT

Intramolecular nucleophilic displacement compound or a precursor thereof wherefrom during photographic processing a photographically useful group can be split off, said intramolecular nucleophilic displacement compound or precursor thereof corresponding to the following general structure (I):

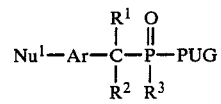

wherein

Nu$^1$ represents a nucelophilic group e.g. HO, H$_2$N or Hs, or a precursor of such nucleophilic group e.g. an oxidized nucleophilic group e.g. O= or HN=, or RO wherein R is an alkyl, an acyl, an aryl or a trialkylsilanyl group, which groups may be substituted, the said nucleophilic group or precursor thereof being located in adjacent position to C(R$^1$R$^2$) so as to make possible elimination of PUG through a nucleophilic displacement reaction;

Ar represents an aryl group or a heteroaryl group (e.g. pyridine), which groups may be substituted by one or more mono-atomic or poly-atomic groups, e.g. alkyl groups, nitro groups, cyano groups, carboxy groups, or by sibstituents which, when in adjacent positions on the ring, together form a ring fused with the (hetero)aryl group, e.g. a benzene ring, a cyclohexane ring, a heteroannulated ring; Ar may comprise as substituent e.g. another nucleophilic group Nu$^2$ (same as or different from Nu$^1$);

each of R$^1$ and R$^2$ (same or different) represents hydrogen or an alkyl, an aryl or an aralkyl group which groups each may be substituted;

R$^3$ represents an alkyl, an aralkyl, an alkyloxy, an aryloxy, an alkylthio, an arylthio, an amino group which groups each may be substituted, an oxy (O$^-$) or a hydroxy group;

PUG is a group containing a hetero atom (selected from among N, S and O) through which it is attached to the phosphor atom and producing a photographically useful activity after cleavage of the bond between the hetero atom and the phosphor atom.

13 Claims, No Drawings

INTRAMOLECULAR NUCLEOPHILIC DISPLACEMENT COMPOUND AND USE IN PHOTOGRAPHY

The present invention relates to compounds capable of releasing a photographically useful group as a result of an intramolecular nucleophilic displacement reaction and to photographic materials containing such compounds.

The term "intramolecular nucleophilic displacement" (IND) is understood to refer to a reaction in which a nucleophilic center on a certain molecule attacks another site (i.e., an electrophilic center) of the same molecule, causing the displacement of a group or atom linked at the electrophilic center. That is, the electrophilic center should be capable of forming a ring structure in combination with the nucleophilic center, preferably a 3- or 5- to 7-membered ring (preferably, a 5- or 6-membered ring).

The term "nucleophilic group" as used herein means an atom or atomic group containing an electron pair capable of forming a covalent bond. This type of group is often an ionizable group which reacts as an anion group. The nucleophilic group can contain at least one atom capable of being a nucleophilic center as in the case of a hydroxylamino group in which either a nitrogen atom or an oxygen atom can become a nucleophilic center.

The term "electrophilic group" as used herein means an atom or atomic group which can receive an electron pair for the formation of a covalent bond. Typical examples of such electrophilic groups are sulfonyl (—SO$_2$), carbonyl (—CO), and thiocarbonyl (—CS). The carbon atom of the (thio)carbonyl group or the sulfur atom of the sulfonyl group can form an electrophilic center for the group and receive partially a positive charge.

Intramolecular nucleophilic displacement compounds can be used in photographic silver halide materials for overall or imagewise releasing a photographically useful group, particularly during wet-processing or by processing under the influence of heat.

Imagewise release is effected by the use of such compounds that are capable of being converted imagewise during photographic processing from a state wherein they are capable of intramolecular nucleophilic displacement into a state wherein they are incapable of intramolecular nucleophilic displacement or vice versa.

Known compounds contain as an electrophilic cleavage group a carbamic acid derivative as described in U.S. Pat. No. 3,980,479 relating to N-(2,5-dihydroxyphenyl)urethanes which undergo a high rate of cyclization in alkaline media.

In another patent, U.S. Pat. No. 4,199,354, use is made of rapid cyclization of 2-(hydroxylamino)benzamides to benzisoxazoles.

Other examples of intramolecular nucleophilic displacement compounds are given in U.S. Pat. Nos. 4,139,379, 4,248,962 and 4,559,290 and in Japanese unexamined patent publications Nos. 60214358, 60230139 and 60237446 and in Angewandte Chemie International Edition in English, Vol. 22(3), 1983, pages 191 to 209, by C. C. Van de Sande.

It is an object of the present invention to provide a class of novel intramolecular nucleophilic displacement compounds.

It is another object of the present invention to provide a photographic material containing such a compound for release of a photographically useful group.

Other objects and advantages will become apparent from the further description.

According to the present invention an intramolecular nucleophilic displacement compound or a precursor thereof is provided wherefrom during photographic processing a photographically useful group can be split off, said intramolecular nucleophilic displacement compound or precursor thereof corresponding to the following general structure (I):

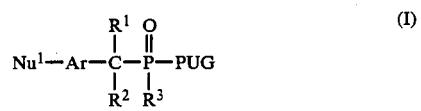

wherein

Nu$^1$ represents a nucleophilic group e.g. HO, H$_2$N or HS, or a precursor of such nucleophilic group e.g. an oxidized nucleophilic group e.g. O= or HN=, or RO wherein R is an alkyl, an acyl, an aryl or a trialkylsilanyl group, which groups may be substituted, the said nucleophilic group or precursor thereof being located in adjacent position to C(R$^1$R$^2$) so as to make possible elimination of PUG through a nucleophilic displacement reaction;

Ar represents an aryl group or a heteroaryl group (e.g. pyridine), which groups may be substituted by one or more mono-atomic or poly-atomic groups, e.g. alkyl groups, nitro groups, cyano groups, carboxy groups, or by substituents which, when in adjacent positions on the ring, together form a ring fused with the (hetero)aryl group, e.g. a benzene ring, a cyclohexane ring, a heteroannulated ring; Ar may comprise as substituent e.g. another nucleophilic group Nu$^2$ (same as or different from Nu$^1$);

each of R$^1$ and R$^2$ (same or different) represents hydrogen or an alkyl, an aryl or an aralkyl group which groups each may be substituted;

R$^3$ represents an alkyl, an aralkyl, an alkyloxy, an aryloxy, an alkylthio, an arylthio, an amino group which groups each may be substituted, an oxy (O$^-$) or a hydroxy group;

PUG is a group containing a hetero atom (selected from among N, S and O) through which it is attached to the phosphor atom and producing a photographically useful activity after cleavage of the bond between the hetero atom and the phosphor atom.

The PUG (photographically useful group) may be a dye, a dye precursor, a base, an acid or any other photographic reagent or precursor thereof. Typical useful photographic reagents are known in the art, e.g. as described in U.S. Pat. Nos. 3,227,551, 3,364,022, 3,379,529 and 3,698,898 and include e.g. a silver complexing agent, a silver halide solvent, a fixing agent, a toning agent, a hardening agent, a fogging agent, an antifogging agent, a sensitizing agent, a desensitizing agent, a developing agent, a precursor of a developing agent, an oxidizing agent, a development inhibitor or restrainer, a development accelerator, a bleach inhibitor, a bleach accelator, a mordanting agent, an image stabilizing agent, a contrast increasing agent, an optical whitening agent, an ultraviolet absorbing agent, a surface active agent, etc.

The PUG may be a conventional dye or a shifted dye. Dye materials of this type are well-known in the art and include azo dyes, azomethine (imine) dyes, anthraquinone dyes, alizarine dyes, merocyanine dyes, quinoline dyes, cyanine dyes and the like. The shifted dyes include those compounds whose light-absorption characteristics are shifted hypsochromically or bathochromically when subjected to a different environment such as a change in pH, a reaction with a material to form a complex, a tautomerization, a reaction to change the pKa of the compound, a removal of a group such as a hydrolyzable acyl group connected to an atom of the chromophore as mentioned in U.S. Pat. No. 3,260,597, and the like.

In another embodiment the compounds of this invention contain as PUG an image dye-providing moiety, which is an image dye precursor. The term "image dye precursor" is understood to refer to those compounds that undergo reactions encountered in a photographic imaging system to produce an image dye such as color couplers, oxichromic compounds and the like. Color couplers can be made to react with an oxidized color developer such as an oxidized primary aromatic amine to form the image dye. Typical useful color couplers include the pyrazolone couplers, pyrazolotriazole couplers, open-chain ketomethylene couplers, phenolic couplers and the like. Further reference to the description of appropriate couplers is found in U.S. Pat. No. 3,620,747, which is incorporated herein by reference. Oxichromic compounds are those compounds that undergo chromogenic oxidation to form the respective image dye. The oxidation can be carried out by aerial oxidation, incorporation of oxidants into the photographic element or film unit or use of an oxidant during processing. Compounds of this type have been referred to in the art as leuco compounds, i.e., compounds that have no color. Typical useful oxichromic compounds include leuco indoanilines, leuco indophenols, leuco anthraquinones and the like.

The PUG can likewise be a silver halide development inhibitor including triazoles and tetrazoles such as a 1-phenyl-5-mercaptotetrazole, a 5-methylbenzotriazole, a 4,5-dichlorobenzotriazole and the like, and it can also be an antifogging agent including besides mercapto compounds azaindenes such as a tetrazaindene and the like.

The photographically useful group can also be a silver halide development accelerator such as a benzylalcohol or a benzyl-α-picoliniumbromide, a fogging agent including hydrazines and hydrazides such as acetylphenylhydrazine and the like, or a developing agent such as a hydroquinone, a p-phenylenediamine, a 1-phenyl-3-pyrazolidinone, ascorbic acid and the like.

When a p-phenylenediamine compound is released from the intramolecular nucleophilic displacement compound according to the present invention, this released developing agent after oxidation can couple with a conventional coupler compound when present in a photographic color material. When the IND compound is a phenolic compound the released p-phenylenediamine can also couple with the residual phenolic compound to form a dye except when the auto-coupling is prevented e.g. when the IND compound is p-alkyl substituted and only coupling with a present conventional coupler compound can take place.

Also an alkaline substance can be released as photographically useful group, e.g. guanidine; piperidine; pyrolidine; $R'_2N^-$, $R'O^-$ or $R'S^-$ in which $R'$ represents an alkyl group, and the like.

In one or more of the substituents $R^1$, $R^2$ and $R^3$ or in a substituent of Ar, a ballasting group may be present. Ballasting groups are groups which allow the compounds according to the invention to be incorporated in a non-diffusing form in the hydrophilic colloid layers normally used in photographic materials. The nature of the ballast group is not critical as long as it confers non-diffusibility to the compound. Since the diffusion properties depend on the molecular size of the compound as a whole, it may be possible in the case of compounds having a high molecular weight that only one or a few short-chain groups confer a satisfactory resistance to diffusion. Typical ballast groups include long-chain alkyl radicals having at least 8 and as many as about 30 carbon atoms and which may also carry isocyclic or heterocyclic or aromatic groups. These residues are attached directly or indirectly to the molecule. The residue which confers diffusion resistance may in addition carry groups conferring solubility in water, e.g. sulfo groups or carboxyl groups, and these may also be present in an anionic form.

The compounds, according to the present invention, are incorporated in a photographic light-sensitive material in a form in which they are stable during the preservation of a photographic light-sensitive material and so that a PUG is released at a desired time during processing of the exposed photographic light-sensitive material.

For example, from a compound according to the present invention a base can be released at the appropriate moment by applying heat, as is illustrated by the following scheme.

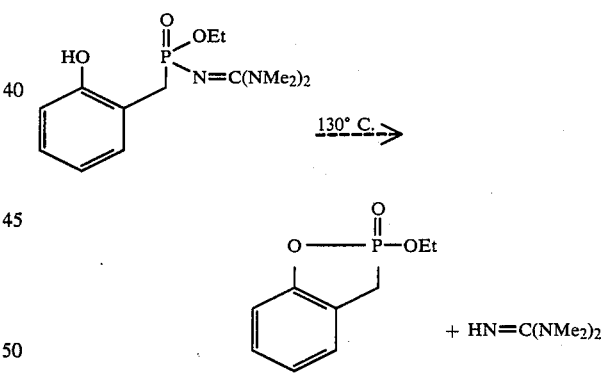

The compounds of the invention can contain substituents which change the rate of cyclization, e.g. initiating cyclization and concomitant PUG-release by alkaline hydrolysis at room temperature in a pH range of from 8 to 13.

The kinetics of the system can be tuned to a limited extent by shielding the nucleophilic center in $Nu^1$, i.e., by the use for $Nu^1$ of a precursor of a nucleophilic group as referred to hereinbefore. The mechanism operative in the release of a PUG from such compound consists of two stages (a) and (b): a first stage wherein the nucleophilic group $Nu^1$ is set free and a second stage wherein the PUG is released.

The following reaction shceme is illustrative of such a two stage release: upon coupling with oxidized color developer the intramolecular nucleophilic displacement compound is released (a); subsequent intramolecular reaction is required to release the PUG (b).
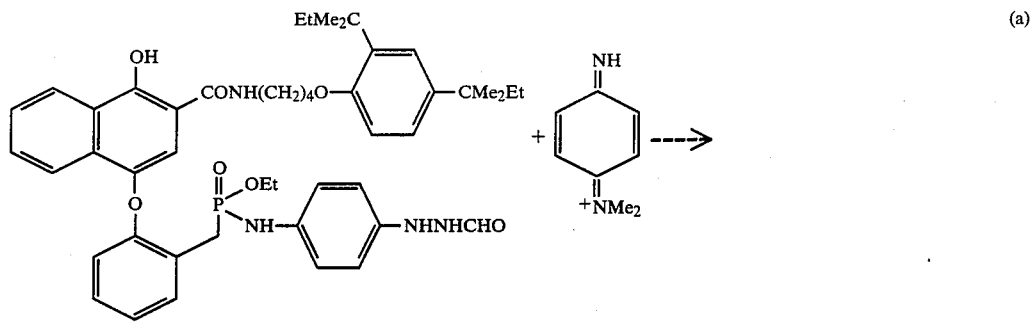
(a)
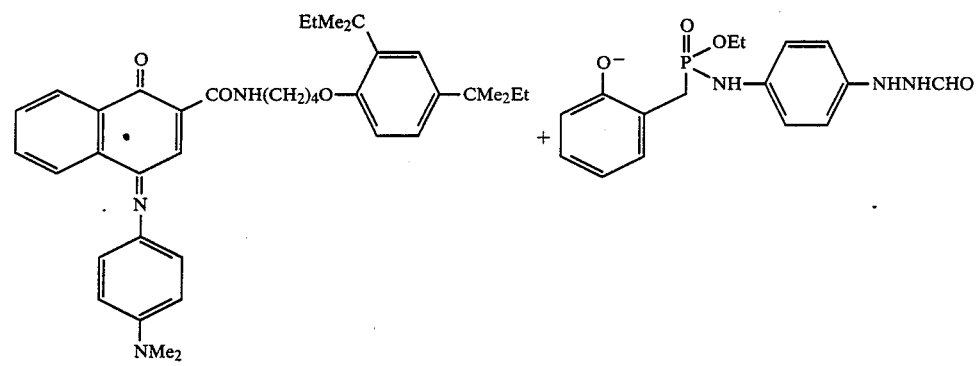
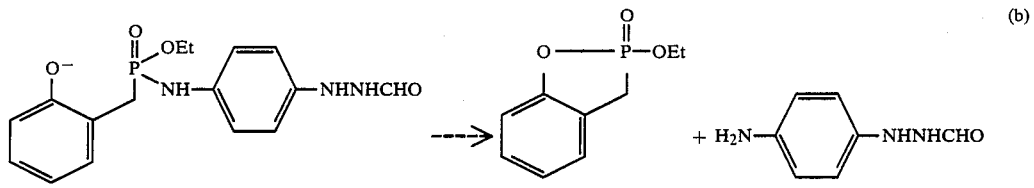
(b)
Another example, according to the mechanism described in European Pat. No. 198,438, is given hereinafter: after oxidation of the hydroquinone nucleus (a1), the IND compound is released by an alkaline substitution reaction (a2) which in its turn releases the PUG (b).
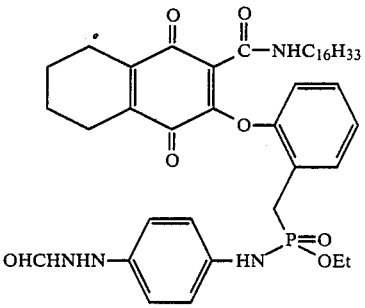
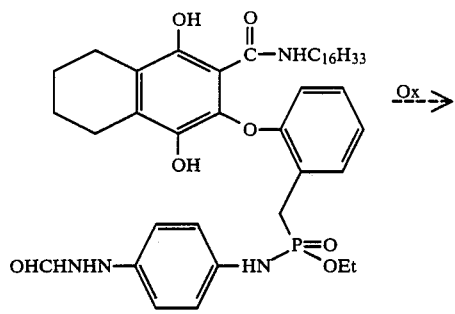
(a1)
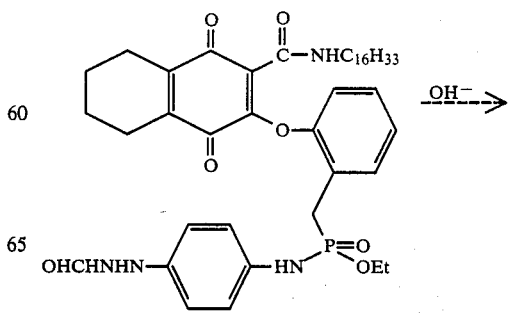
(a2)

-continued

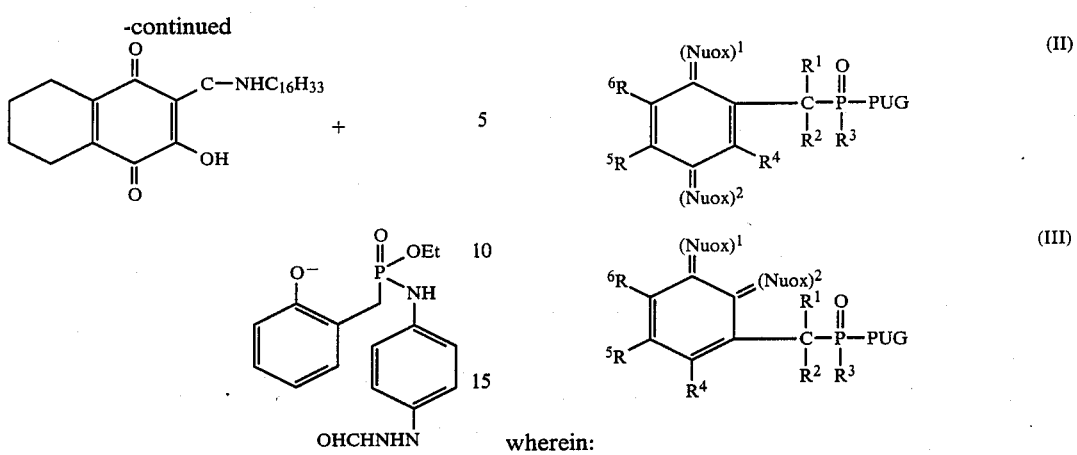

Particular useful PUG-providing compounds of the present invention are those compounds that in oxidized form are stable but in reduced state set free a PUG moiety under alkaline conditions by the intramolecular nucleophilic displacement reaction in accordance with the invention. Compounds of this type can be used in reduced form in an unexposed light-sensitive material and are called IHO-compounds, IHO being an acronym for "Inhibited Hydrolysis by Oxidation". When used in the oxidized form these compounds are called IHR-compounds, wherein IHR is the acronym for "Increased Hydrolysis by Reduction".

Preferred IHR-compounds according to the invention, which are initially immobile in an alkali-permeable colloid medium and wherefrom through the reducing action of a silver halide developing agent and alkalinity a photographically useful group can be split off in diffusible state correspond to one of the following general formulae (II) and (III):

wherein:
each of (Nuox)$^1$ and (Nuox)$^2$ (same or different) represents an oxidized nucleophilic group e.g. O or HN;

each of $R^4$, $R^5$ and $R^6$ represents a mono-atomic group e.g. hydrogen, a halogen atom, or a poly-atomic group e.g. an alkyl group, a substituted alkyl group, an aryl group, a substituted aryl group, an alkyloxy group, a substituted alkyloxy group, an alkylthio group, a substituted alkylthio group, an acylamino group wherein the acyl group is derived from aliphatic or aromatic carboxylic or sulfonic acids, or $R^4$ and $R^5$ together when in adjacent positions on the ring form a ring fused with the remainder of the molecule, e.g. a benzene, a cyclohexane or a heteroannulated ring, or $R^5$ and $R^6$ together form a ring fused with the remainder of the molecule, e.g. a benzene, a cyclohexane or a heteroannulated ring.

Preferably in at least one of the substituents $R^1$, $R^2$, $R^3$, $R^4$, $R^5$ and $R^6$ a ballasting group, e.g. alkyl group of sufficient size, is present to render said compound immobile in an alkali-permeable layer of the photographic material.

The reaction mechanism followed in the release of a PUG by said compounds is illustrated by simplified general formulae as follows:

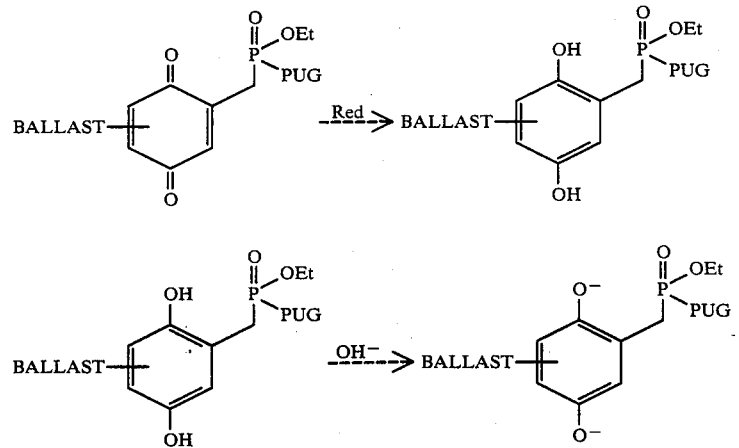

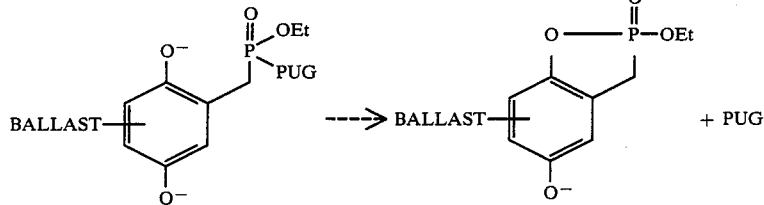

Particular useful IHR-compounds according to the present invention are those compounds wherein the photographically useful group after release represents a dye. In these compounds -PUG in the above general formulae (II) and (III) can be represented by -X-DYE wherein X preferably represents

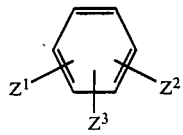

wherein:
each of $Z^1$ and $Z^2$ (same or different) represents a linking O, NH, $SO_2$, $SO_3$, CO, $CO_2$ or $NHSO_2$;
$Z^3$ represents hydrogen or a solubilizing group, e.g. $SO_3H$, $CO_2H$ or NHMe.

Representatives of intramolecular nucleophilic displacement compounds according to the present invention are listed in the following table.

TABLE 1

(A)

| -BASE | $R^{14}$ | $R^{7A}$ | |
|---|---|---|---|
| —$Net_2$ | H | H | (A1) |
| | | Me | (A2) |
| | | $NO_2$ | (A3) |
| | | CN | (A4) |
| | | COOH | (A5) |
| | | $CMe_2CH_2CMe_3$ | (A6) |
| | Me | H | (A7) |
| | | Me | (A8) |
| | | $NO_2$ | (A9) |
| | | CN | (A10) |
| | | COOH | (A11) |
| | | $CMe_2CH_2CMe_3$ | (A12) |
| —N⟨ring⟩ (6-mem) | H | H | (A13) |
| | | Me | (A14) |
| | | $NO_2$ | (A15) |
| | | CN | (A16) |
| | | COOH | (A17) |
| | | $CMe_2CH_2CMe_3$ | (A18) |
| | Me | H | (A19) |
| | | Me | (A20) |
| | | $NO_2$ | (A21) |
| | | CN | (A22) |
| | | COOH | (A23) |
| | | $CMe_2CH_2CMe_3$ | (A24) |
| —N⟨ring⟩ (4-mem) | H | H | (A25) |
| | | Me | (A26) |
| | | $NO_2$ | (A27) |
| | | CN | (A28) |
| | | COOH | (A29) |
| | | $CMe_2CH_2CMe_3$ | (A30) |
| | Me | H | (A31) |

TABLE 1-continued (A)

| -BASE | $R^{14}$ | $R^{7A}$ | |
|---|---|---|---|
| | | Me | (A32) |
| | | $NO_2$ | (A33) |
| | | CN | (A34) |
| | | COOH | (A35) |
| | | $CMe_2CH_2CMe_3$ | (A36) |
| —$N(CHMe_2)_2$ | H | H | (A37) |
| | | Me | (A38) |
| | | $NO_2$ | (A39) |
| | | CN | (A40) |
| | | COOH | (A41) |
| | | $CMe_2CH_2CMe_3$ | (A42) |
| | Me | H | (A43) |
| | | Me | (A44) |
| | | $NO_2$ | (A45) |
| | | CN | (A46) |
| | | COOH | (A47) |
| | | $CMe_2CH_2CMe_3$ | (A48) |
| —$NHC_6H_{13}$ | H | H | (A49) |
| | | Me | (A50) |
| | | $NO_2$ | (A51) |
| | | CN | (A52) |
| | | COOH | (A53) |
| | | $CMe_2CH_2CMe_3$ | (A54) |
| | Me | H | (A55) |
| | | Me | (A56) |
| | | $NO_2$ | (A57) |
| | | CN | (A58) |
| | | COOH | (A59) |
| | | $CMe_2CH_2CMe_3$ | (A60) |
| —$N(C_3H_7)_2$ | H | H | (A61) |
| | | Me | (A62) |
| | | $NO_2$ | (A63) |
| | | CN | (A64) |
| | | COOH | (A65) |
| | | $CMe_2CH_2CMe_3$ | (A66) |
| | Me | H | (A67) |
| | | Me | (A68) |
| | | $NO_2$ | (A69) |
| | | CN | (A70) |
| | | COOH | (A71) |
| | | $CMe_2CH_2CMe_3$ | (A72) |
| —$N=C(NH_2)_2$ | H | H | (A73) |
| | | Me | (A74) |
| | | $NO_2$ | (A75) |
| | | CN | (A76) |
| | | COOH | (A77) |
| | | $CMe_2CH_2CMe_3$ | (A78) |
| | Me | H | (A79) |
| | | Me | (A80) |
| | | $NO_2$ | (A81) |
| | | CN | (A82) |
| | | COOH | (A83) |
| | | $CMe_2CH_2CMe_3$ | (A84) |
| —$N=C(NMe_2)_2$ | H | H | (A85) |
| | | Me | (A86) |
| | | $NO_2$ | (A87) |
| | | CN | (A88) |
| | | COOH | (A89) |

TABLE 1-continued

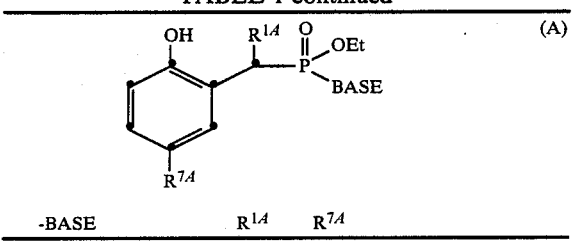
(A)

| -BASE | $R^{14}$ | $R^{7A}$ |
|---|---|---|
| | Me | $CMe_2CH_2CMe_3$ (A90) |
| | | H (A91) |
| | | Me (A92) |
| | | $NO_2$ (A93) |
| | | CN (A94) |
| | | COOH (A95) |
| | | $CMe_2CH_2CMe_3$ (A96) |

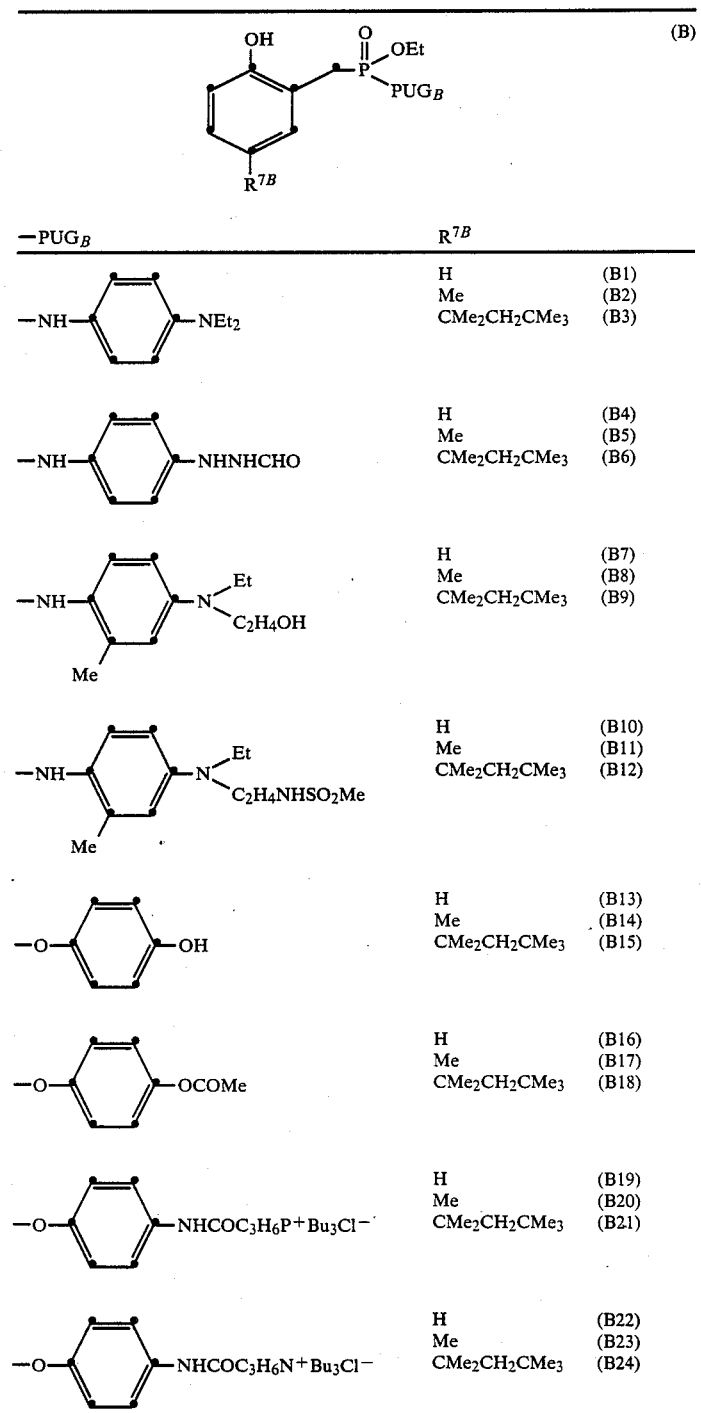
(B)

| —$PUG_B$ | $R^{7B}$ | |
|---|---|---|
| —NH—⟨⟩—NEt₂ | H | (B1) |
| | Me | (B2) |
| | $CMe_2CH_2CMe_3$ | (B3) |
| —NH—⟨⟩—NHNHCHO | H | (B4) |
| | Me | (B5) |
| | $CMe_2CH_2CMe_3$ | (B6) |
| —NH—⟨⟩—N(Et)(C₂H₄OH), Me | H | (B7) |
| | Me | (B8) |
| | $CMe_2CH_2CMe_3$ | (B9) |
| —NH—⟨⟩—N(Et)(C₂H₄NHSO₂Me), Me | H | (B10) |
| | Me | (B11) |
| | $CMe_2CH_2CMe_3$ | (B12) |
| —O—⟨⟩—OH | H | (B13) |
| | Me | (B14) |
| | $CMe_2CH_2CMe_3$ | (B15) |
| —O—⟨⟩—OCOMe | H | (B16) |
| | Me | (B17) |
| | $CMe_2CH_2CMe_3$ | (B18) |
| —O—⟨⟩—NHCOC₃H₆P⁺Bu₃Cl⁻ | H | (B19) |
| | Me | (B20) |
| | $CMe_2CH_2CMe_3$ | (B21) |
| —O—⟨⟩—NHCOC₃H₆N⁺Bu₃Cl⁻ | H | (B22) |
| | Me | (B23) |
| | $CMe_2CH_2CMe_3$ | (B24) |

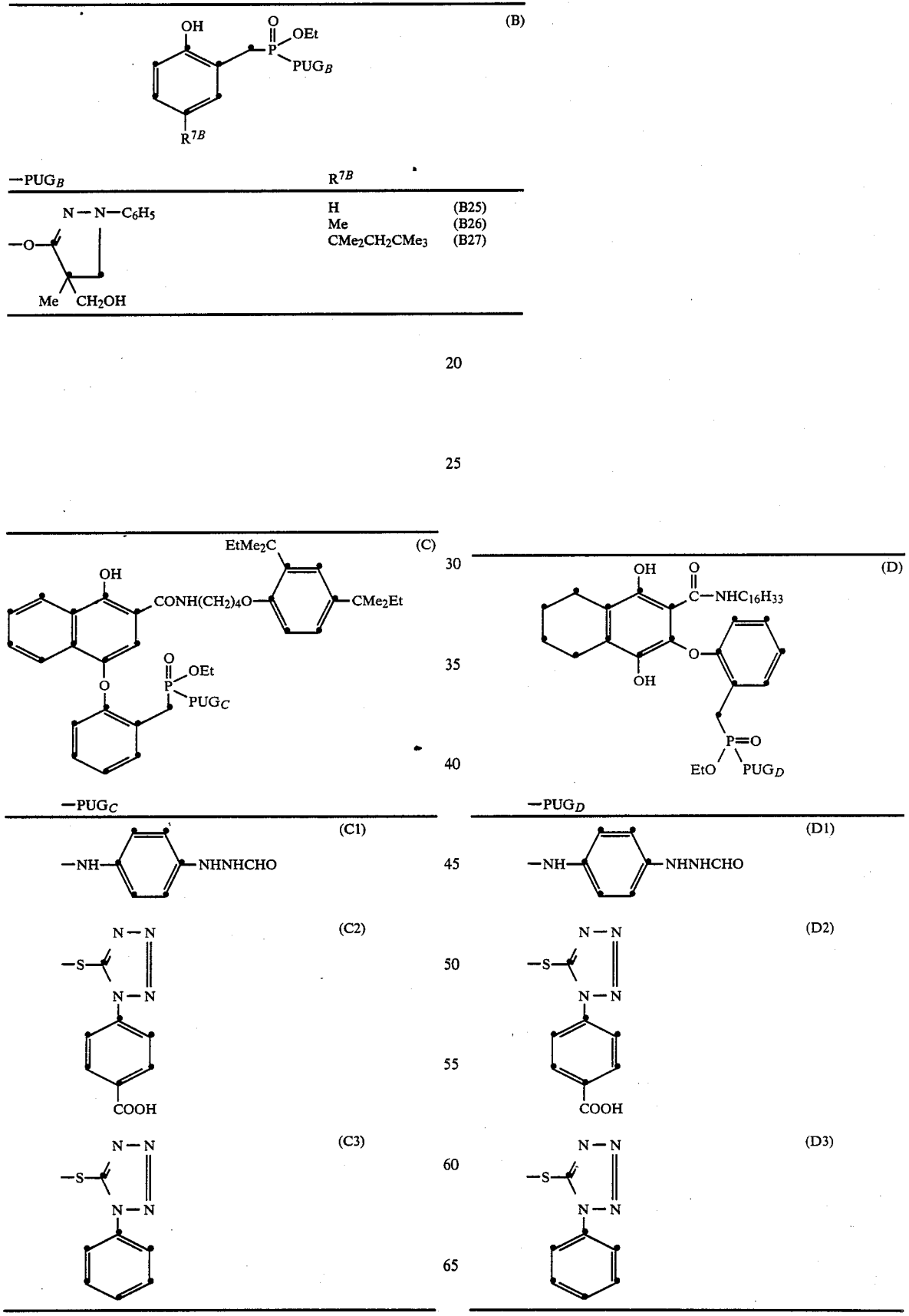

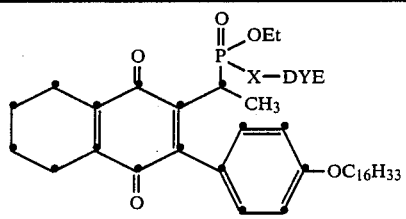
(E)
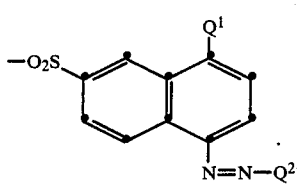
-DYE₁
| —X— | Q¹ | —Q² | |
|---|---|---|---|
| 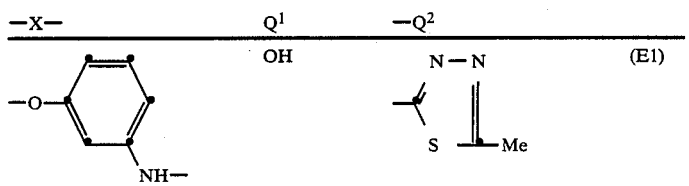 | OH | | (E1) |
| | NHSO₂Me | | (E2) |
| | OH | | (E3) |
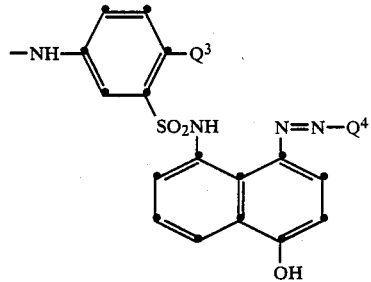
-DYE₂
| —X— | Q³ | —Q⁴ | |
|---|---|---|---|
| 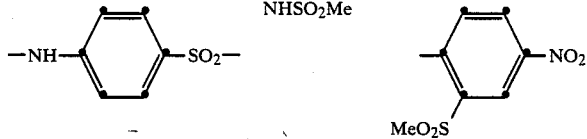 | NHSO₂Me | | (E4) |
| 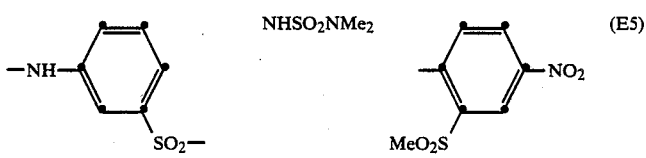 | NHSO₂NMe₂ | | (E5) |

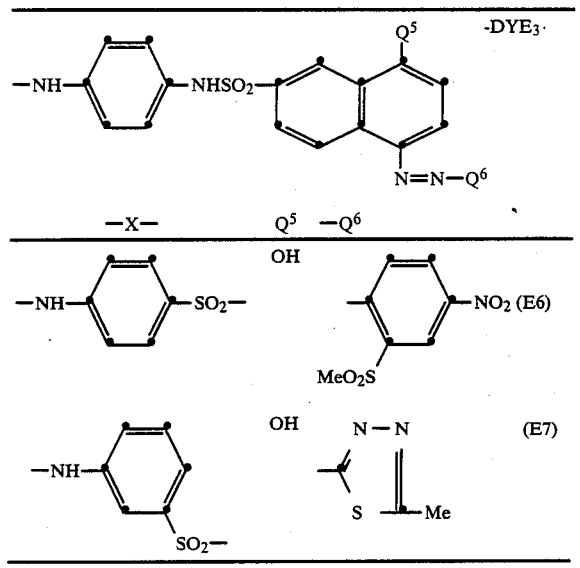

| —X— | $Q^5$ | —$Q^6$ |
|---|---|---|
| —NH—⬡—SO$_2$— | OH on naphthalene | —⬡—NO$_2$ (E6) with MeO$_2$S |
| —NH—⬡—SO$_2$— | OH | (E7) thiadiazole-Me |

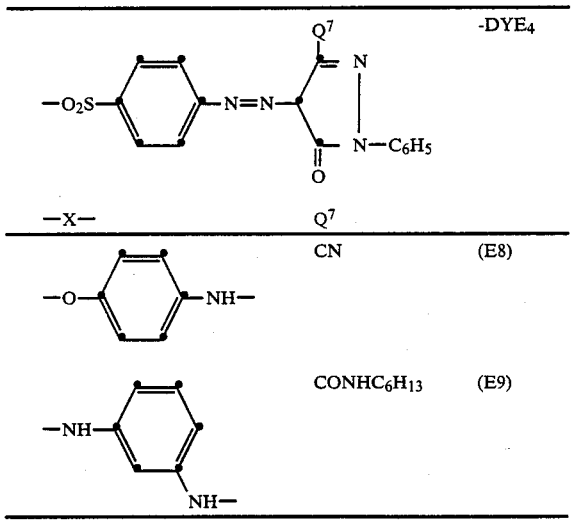

| —X— | $Q^7$ |
|---|---|
| —O—⬡—NH— | CN (E8) |
| —NH—⬡—NH— | CONHC$_6$H$_{13}$ (E9) |

The preparation of some particularly useful compounds according to the present invention is described in the following by way of example. Other compounds for use according to the present invention can be prepared analogously or by techniques known in the art starting with the appropriate chemicals.

PREPARATION OF COMPOUND A1

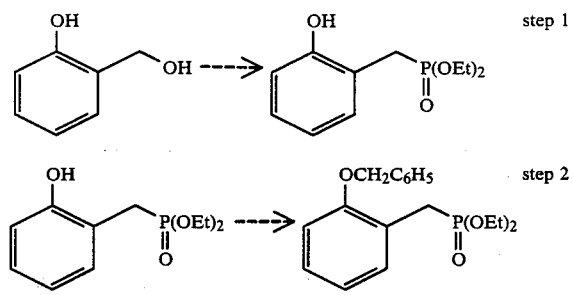

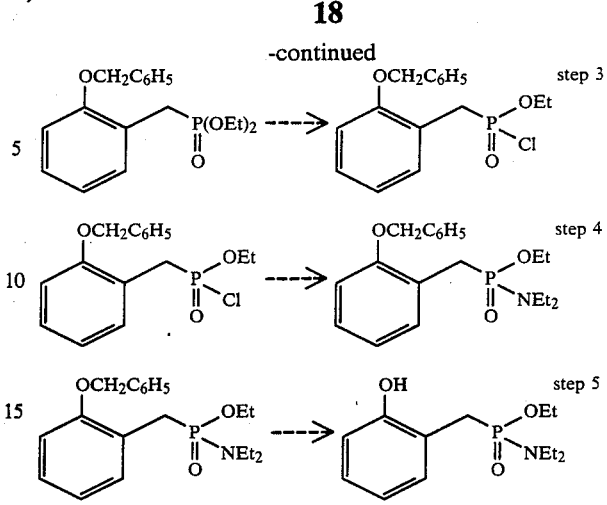

Step 1

2-Hydroxymethylphenol (0.81 mole, 100 g) was dissolved together with triethylphosphite (0.81 mole, 134.7 g) in dimethylformamide (338 ml). The solution was slowly heated to reflux (105° C.). The reaction proceeded exothermally whereupon the reaction mixture was heated at 135°–140° C. for 4–5 hours.

Step 2

To the obtained solution of (o-hydroxyphenyl)methyl phosphonic acid diethyl ester in dimethylformamide, diluted with ethanol (dimethylformamide/ethanol 1:10), 241.5 g of potassium carbonate (2.1 eq., 1.75 mole) were added. Into this suspension benzylbromide (0.81 mole, 95.75 ml) was introduced dropwise at room temperature within one hour. After 4 hours stirring with reflux at room temperature potassium carbonate was filtered off and the filtrate concentrated under reduced pressure and poured out into 2 l of dichloromethane. The solution was alkalified by washing with a saturated sodium carbonate solution, consecutively neutralized with a saturated sodium chloride solution, dried with sodium sulfate and, after removal of the sodium sulfate, concentrated under reduced pressure. The residual oil was purified by chromatography using as eluent a mixture of methylene chloride and ethyl acetate 7:3. Yield of the crude product: 250.2 g (93%). Yield of (o-benzyloxyphenyl)methyl phosphonic acid diethyl ester after purification: 151.1 g (56%).

Step 3

7.84 ml of oxalylchloride (3 eq., 0.0897 mole), dissolved in 9 ml of dry dichloromethane, were added dropwise under nitrogen atmosphere and at 0° C. to a solution of the phosphonic acid diethyl ester of the previous step (0.0299 mole, 10 g) in dry dichloromethane (45 ml). The obtained solution was refluxed at 50°–60° C. for 3–5 hours. When the evolution of gas was finished, the solution was concentrated under reduced pressure. After addition of toluene (100 ml) the solution was again concentrated under reduced pressure. Yield of (o-benzyloxyphenyl)methyl phosphonic acid chloride monoethyl ester: 9.0 g (93%).

Step 4

A solution of 3 g of (o-benzyloxyphenyl)methyl phosphonic acid chloride monoethyl ester (9.24 mmole) in 3 ml of dry toluene was added dropwise at 0° C. and under nitrogen atmosphere to a solution of 2.37 ml of diethylamine (2.4 eq., 0.0225 mole) in 3 ml of dry toluene. The solution was stirred at room temperature and under nitrogen atmosphere for 20 min and then dissolved in 100 ml of dry dichloromethane. The solution was acidified with 10 ml of a 1N hydrochloric acid solution, alkalified with a saturated sodium hydrogen carbonate solution (10 ml) and neutralized with a saturated sodium chloride solution. The organic phase was dried with sodium sulfate and thereupon, after removal of the sodium sulfate, the filtrate was concentrated under reduced pressure. The residue was purified by chromatography with methylene chloride/methanol mixture (95:5) as an eluent. Yield of the crude product: 2.7 g (81%). Yield of (o-benzyloxyphenyl)methyl phosphonic acid diethylamino monoethyl ester after purification: 700 mg (21%).

Step 5

2.4 g of (o-benzyloxyphenyl)methyl phosphonic acid diethylamino monoethyl ester (6.65 mmole) was dissolved in 100 ml of ethyl acetate containing 1 g of 5% Pd-C as a catalyst. After one hour of stirring the reaction mixture at room temperature and under hydrogen atmosphere (1 atm) the catalyst was filtered off and washed througly with ethyl acetate. The filtrate was concentrated under reduced pressure and the residual oil purified by chromatography using as eluent a mixture of methylene chloride and methanol 98:2. Yield of the crude product: 1.7 g (94%). Yield of A1 after purification: 620 mg (34%).

hour to a suspension of lithiumaluminiumhydride (1.02 eq., 28.7 g) in tetrahydrofuran (concentration 0.5M). At the completion of the reaction the suspension obtained was cooled down at 0° C. whereupon 28.7 ml of water, 28.7 ml of a 15% sodium hydroxide solution and 86.1 ml of water were slowly added successively. After filtration, 3 to 4 l of methylene chloride were added to the filtrate. The organic phase was neutralized by washing with a saturated sodium chloride solution and dried with sodium sulfate. Thereupon after removal of the sodium sulfate the filtrate was concentrated under reduced pressure and an oily residue was obtained. Yield of 2-(1'-hydroxy)ethylphenol: 85.3 g (84%).

Step 2

72.2 g of the 2-(1'-hydroxy)ethylphenol (0.52 mole) were dissolved in 218 ml of dimethylformamide. After addition of triethylphosphite (0.52 mole, 92.96 ml), the reaction mixture was boiled with reflux for 2 to 3 hours. The liberated ethanol was removed during the reaction by distillation. The end of the reaction was established by thin-layer chromatography.

Step 3

To the obtained solution of (1-methyl,1-o-hydroxyphenyl)methyl phosphonic acid diethyl ester in dimethylformamide, diluted with ethanol (dimethylformamide/ethanol 1:10), 151.6 g of potassium carbonate (2.1 eq., 1.099 mole) were added. Into this suspension benzylbromide (1 eq., 0.5232 mole, 62.13 ml) was introduced dropwise within one hour at 40°–50° C. under

PREPARATION OF COMPOUND A7

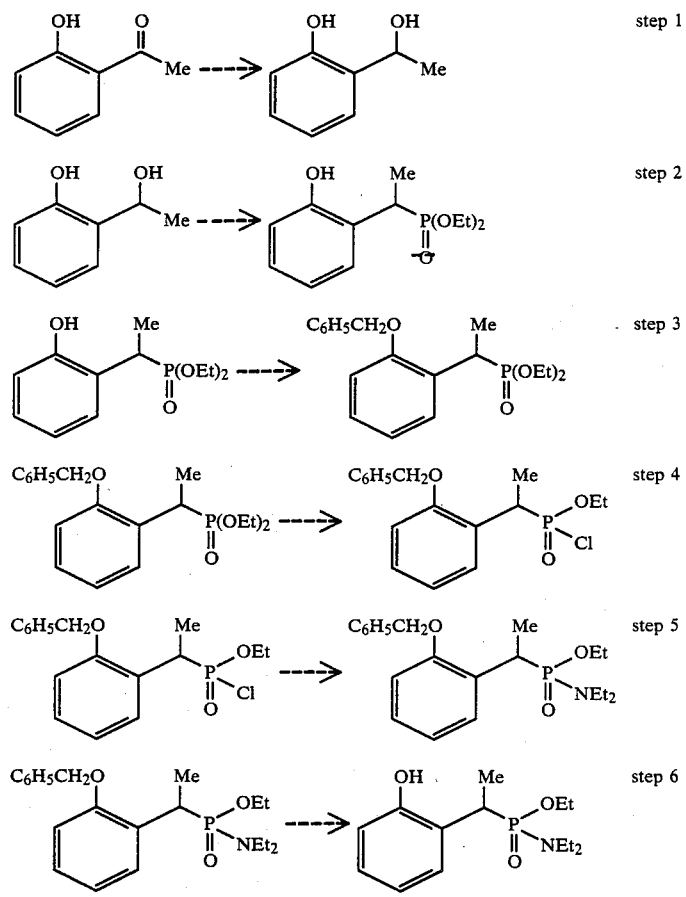

Step 1

At room temperature 88.48 ml of o-hydroxyacetofenon (0.7353 mole) were added dropwise within one reflux. After stirring for 5 to 6 hours at 45°–50° C. the potassium carbonate was filtered off and the filtrate concentrated under reduced pressure and poured out into 3 l of dichloromethane. The organic phase was neutralized by washing with a saturated sodium chloride solution, dried with sodium sulfate and, after removal of the sodium sulfate, concentrated under reduced pressure. Dimethylformamide, triethylphosphite and benzylbromide were removed by vacuum distillation. The residue was purified by chromatography using as eluent a mixture of methylene chloride and ethyl acetate 8:2. Yield of the crude product: 149.7 g (83%). Yield of (1-methyl,1-o-benzyloxyphenyl)methyl phosphonic acid diethyl ester after purification: 76 g (42%).

Step 4

60.90 ml of oxalychloride (3 eq., 0.699 mole), dissolved in 70 ml of dry dichloromethane, were added dropwise under nitrogen atmosphere and at 0° C. in a period of 10 minutes to a solution of the phosphonic acid diethyl ester of the previous step (0.233 mole, 81.1 g) in dry dichloromethane (349 ml). The obtained yellow colored solution was refluxed at 50°-60° C. for 20-25 hours. When the evolution of gas was finished, the solution was concentrated under reduced pressure. After addition of toluene (2×100 ml) the solution was again concentrated under reduced pressure. Yield of (1-methyl,1-o-benzyloxyphenyl)methyl phosphonic acid chloride monoethyl ester: 57.3 g (72%).

Step 5

A solution of 11.5 g of (1-methyl,1-o-benzyloxyphenyl)methyl phosphonic acid chloride monoethyl ester (0.0340 mole) in 12 ml of dry toluene was added dropwise at 0° C. and under nitrogen atmosphere to a solution of 6.32 g of diethylamine (0.0866 mole) in 7 ml of dry toluene. The solution was stirred at room temperature and under nitrogen atmosphere for 24 hours and then poured out into 350 ml of dichloromethane. The solution was acidified with 50 ml of a 1N hydrochloric acid solution, alkalified with a saturated sodium hydrogen carbonate solution and neutralized with a saturated sodium chloride solution. The organic phase was dried with sodium sulfate and thereupon, after removal of the sodium sulfate, the filtrate was concentrated under reduced pressure. The oily residue was purified by chromatography with methylene chloride/methanol mixture (98:2) as an eluent. Yield of the crude product: 11.4 g (89%). Yield of (1-methyl,1-o-benzyloxyphenyl)methyl phosphonic acid diethylamino monoethyl ester after purification: 8.1 g (64%).

Step 6

7.8 g of (1-methyl,1-o-benzyloxyphenyl)methyl phosphonic acid diethylamino monoethyl ester (0.0208 mole) was dissolved in 100 ml of ethyl acetate containing 1 g of 5% Pd-C as a catalyst. After 2 hours of stirring the reaction mixture at room temperature and under hydrogen atmosphere (1 atm) the catalyst was filtered off and washed througly with ethyl acetate. The filtrate was concentrated under reduced pressure and the residual oil purified by chromatography using as eluent a mixture of methylene chloride and methanol 95:5. Yield of the crude product: 5 g (84%). Yield of A7 after purification: 2.50 g (42%).

PREPARATION OF COMPOUND A13

This compound was prepared in an analogeous manner as compound A1. Instead of diethylamine, piperidine was used.

PREPARATION OF COMPOUND A18

This compound was prepared in an analogeous manner as compound A1 except for differences stated in the following procedure.

In a 3 liter flask 50.7 g of lithiumaluminiumhydride were introduced and 575 ml of tetrahydrofuran were added with cooling in ice-water. A solution of 316.9 g (1.27 mole) of 2-hydroxy,5-(1',1',3',3'-tetramethylbutyl) benzoic acid was added dropwise while stirring and cooling. The mixture was stirred for 45 minutes at 10° C. and subsequently for 3 hours at 70° C. with reflux. A further amount of 25.4 g of lithiumaluminiumhydride in 250 ml of tetrahydrofuran was added and the mixture was stirred for 6 hours at 70° C. Tetrahydrofuran (1000 ml) was distilled off and the reaction mixture was cooled and acidified with a hydrochloric acid solution. To facilitate filtration by suction diatomaceous earth was added. After filtration and washing with dichloromethane and saturated sodium chloride solution, the organic phase was dried on sodium sulfate and after suction filtering concentrated. Yield of the crude product: 275.1 g (92%). Yield of 2-hydroxymethyl,4-(1',1',3',3'-tetramethylbutyl)phenol after purification by preparative column chromatography: 178.5 g.

Step 1

2-Hydroxymethyl,4-(1',1',3',3'-tetramethylbutyl)-phenol (0.110 mole, 26 g) was dissolved in dimethylformamide (44 ml) whereupon triethylphosphite (1.05 eq., 19.8 ml) was added. This mixture was heated to a temperature of 100° C. in a reaction flask provided with a downward fitted Liebig's condenser for distillation of the liberated ethanol. After 4 h 30 min 0.05 eq. (0.94 ml) of triethylphosphite were added and the solution was kept at 100° C. for 1 h 15 min.

Step 2

To the obtained solution of 0.110 moles of [2-hydroxy,5-(1',1',3',3'-tetramethylbutyl)phenyl]methyl phosphonic acid diethyl ester in 44 ml of dimethylformamide, 440 ml of ethanol, 31.92 g of potassium carbonate (2.1 eq.) and 13.75 ml (1 eq.) of benzylbromide were added. This reaction mixture was slowly heated to reach a gentle reflux (77° C.) for 16 hours. Thereupon the potassium carbonate was filtered off and after washing with dichloromethane, ethanol was distilled off. 400 ml of dichloromethane were added. The solution was washed with 50 ml of a saturated sodium hydrogen carbonate solution to reach a pH of about 8-9, consecutively with 50 ml of water and 2×50 ml of a saturated sodium chloride solution to reach a pH of 7, dried with sodium sulfate and, after removal of the sodium sulfate, concentrated under reduced pressure. A yellow oil was obtained. Yield of the crude product: 38.2 g (78%). Yield of [2-benzyloxy,5-(1',1',3',3'-tetramethylbutyl)-phenyl]methyl phosphonic acid diethyl ester after purification: 28.3 g (58%).

Step 3

14.77 ml of oxalylchloride (3 eq.), dissolved in 16.8 ml of dry dichloromethane, were added dropwise under nitrogen atmosphere and at 0° C. to a solution of the phosphonic acid diethyl ester of the previous step (56.4 mmole, 25.15 g) in dry dichloromethane (112.5 ml). The obtained solution was refluxed at 40° C. for 5 h 25 min. When the evolution of gas was finished, the solution was concentrated under reduced pressure. After addition of dry toluene the solution was again concentrated under reduced pressure.

Step 4

A solution of 0.056 mole of [2-benzyloxy,5-(1',1',3',3'-tetramethylbutyl)phenyl]methyl phosphonic acid chloride monoethyl ester in 17.8 ml of dry toluene was added dropwise at 0° C. and under nitrogen atmosphere to a solution of 14.14 ml (2.5 eq.) of piperidine in 34 ml of dry toluene. The solution was stirred at 0° C. for 30 minutes and subsequently at room temperature for 1 hour. A white precipitate was formed. 150 ml of dichloromethane were added and the solution was washed with 2×100 ml of a 1N hydrochloric acid solution, with 100 ml of a saturated sodium hydrogen carbonate solution and with 100 ml of a saturated sodium chloride solution. The organic phase was dried with sodium sulfate and thereupon, after removal of the sodium sulfate, the filtrate was concentrated under reduced pressure. Yield of the crude product: 30.29 g. Yield of [2-benzyloxy,5-(1',1',3',3'-tetramethylbutyl)phenyl]methyl phosphonic acid piperidino monoethyl ester after purification: 24.5 g (90%).

Step 5

22.7 g of [2-benzyloxy,5-(1',1',3', 3'-tetramethylbutyl)phenyl]methyl phosphonic acid piperidino monoethyl ester (46.8 mmole) was dissolved in 110 ml of dry ethyl acetate containing 2.8 g of 5% Pd-C as a catalyst. After 19 hours of stirring the reaction mixture at room temperature and under hydrogen atmosphere the catalyst was filtered off and washed thorougly with dichloromethane. The filtrate was concentrated under reduced pressure. Ethyl acetate was added whereupon a white precipitate was obtained. Yield of the crude product: 13.8 g (75%). Yield of A18 after purification: 10 g (54%).

PREPARATION OF COMPOUND A19

This compound was prepared in an analogeous manner as compound A7. Instead of diethylamine, piperidine was used.

PREPARATION OF COMPOUND A25

This compound was prepared in an analogeous manner as compound A1. Instead of diethylamine, pyrrolidine was used.

PREPARATION OF COMPOUND A26

This compound was prepared in an analogeous manner as compound A7. Instead of diethylamine, pyrrolidine was used.

PREPARATION OF COMPOUND A49

This compound was prepared in an analogeous manner as compound A1. Instead of diethylamine, n-hexylamine was used.

PREPARATION OF COMPOUND A61

This compound was prepared in an analogeous manner as compound A1. Instead of diethylamine, dipropylamine was used.

PREPARATION OF COMPOUND A67

This compound was prepared in an analogeous manner as compound A7. Instead of diethylamine, dipropylamine was used.

PREPARATION OF COMPOUND A85

This compound was prepared in an analogeous manner as compound A1. Instead of diethylamine, tetramethylguanidine was used.

PREPARATION OF COMPOUND A91

This compound was prepared in an analogeous manner as compound A7. Instead of diethylamine, tetramethylguanidine was used.

PREPARATION OF COMPOUND B10

This compound was prepared in an analogeous manner as compound A1 except for differences stated in the following procedure.

Step 4

180 g of 2-amino,5-[N-ethyl-N(Beta-methylsulfonamido)ethyl]amino toluene $1.5H_2SO_4.H_2O$ was dissolved in 300 ml of dichloromethane. A saturated sodium hydrogen carbonate solution was added to reach a pH of 8. The reaction mixture was washed with a saturated sodium chloride solution, dried with sodium sulfate and concentrated. This solution was added at 0° C. to a solution of 49 g of (o-benzyloxyphenyl)methyl phosphonic acid chloride monoethyl ester in 49 ml of dry dichloromethane. The solution was extracted with water and with a saturated sodium chloride solution, dried with sodium sulfate whereupon the solvent was evaporated. Yield of the crude product: 82.6 g. After purification by chromatography (eluent: mixture methylene chloride/methanol 90:10) the yield of (o-benzyloxyphenyl)methyl phosphonic acid 4-[N-ethyl-N-(Beta-methylsulfonamido)ethyl]amino,2-methyl-aniline monoethyl ester was 60.5 g (72%).

Step 5

50 g of the phosphonic acid monoethyl ester of the previous step was dissolved in 1.2 l of ethyl acetate and 5 g of 5% Pd-C was added as a catalyst. The reaction mixture was stirred for 15 hours at room temperature under hydrogen atmosphere (3 atm) whereupon the catalyst was filtered off and the reaction mixture concentrated under reduced pressure. Yield of the crude product: 39.7 g. Yield of the compound B10 after purification by column chromatography (eluent: methylene chloride/methanol/hexane 50:5:45): 35 g (84%).

PREPARATION OF COMPOUND B12

This compound was prepared in an analogeous manner as compound A18. Instead of piperidine, 2-amino,5-[N-ethyl-N(Beta-methylsulfonamido)ethyl]amino toluene $1.5H_2SO_4.H_2O$ was used.

PREPARATION OF COMPOUND B16

This compound was prepared in an analogeous manner as compound A1 except for differences stated in the following procedure.

Step 4

A solution of 17.2 g of (o-benzyloxyphenyl)methyl phosphonic acid chloride monoethyl ester (0.053 mole) in 70 ml of dry dichloromethane was added dropwise at 0° C. and under nitrogen atmosphere to a mixture of 8 g (1 eq.) hydroquinone monoacetate, 150 ml of dry dichloromethane and 7.4 ml (1 eq.) of dry triethylamine. The reaction proceeded slightly exothermally and the mixture was stirred at room temperature for 18 hours. 200 ml of dichloromethane were added and the solution was extracted once with water and thereafter twice with a saturated sodium chloride solution. The organic phase was dried on magnesium sulfate and thereupon, after filtration of the magnesium sulfate, the filtrate was concentrated under reduced pressure. The residual yellow oil (24.2 g) was purified by column chromatography and the yield of (o-benzyloxyphenyl)methyl phosphonic acid p-acetyloxyphenyl ethyl diester after purification was 12 g (52%).

Step 5

0.25 g (0.57 mmole) of the phosphonic acid diester of the previous step was dissolved in 2 ml of dry dichloromethane and 0.05 g of 5% Pd-C was added as a catalyst. The reaction mixture was stirred for 2 h 25 min at room temperature under hydrogen atmosphere. By thin layer chromatography it was indicated that the starting product was totally converted into compound B16.

PREPARATION OF COMPOUND B18

This compound was prepared in an analogeous manner as compound B16. Instead of (o-benzyloxyphenyl)-methyl phosphonic acid chloride monoethyl ester, [2-benzyloxy,5-(1′,1′,3′,3′-tetramethylbutyl)phenyl]methyl phosphonic acid chloride monoethyl ester was used.

PREPARATION OF COMPOUND B27

This compound was prepared in an analogeous manner as compound B18. Instead of acetic acid p-phenol ester, 4-hydroxymethyl 4-methylphenidon was used.

PREPARATION OF COMPOUND E2

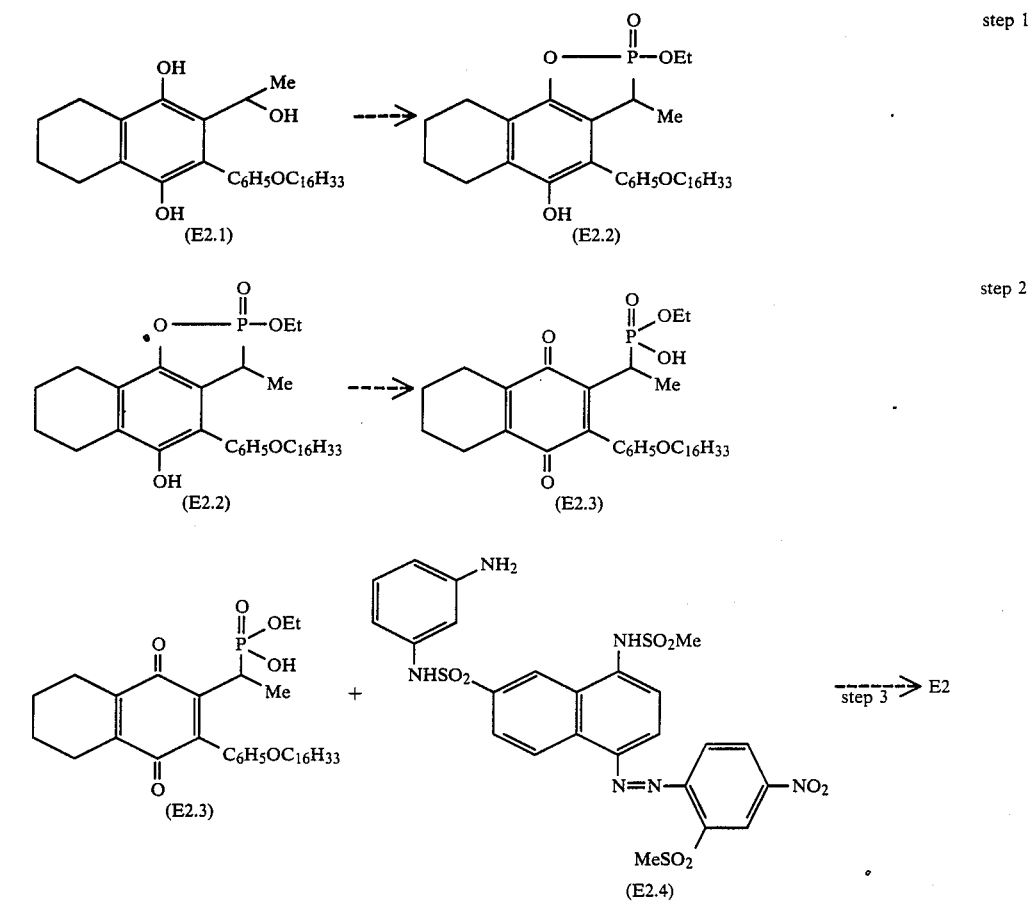

Compound E2.4 was prepared in the following way.

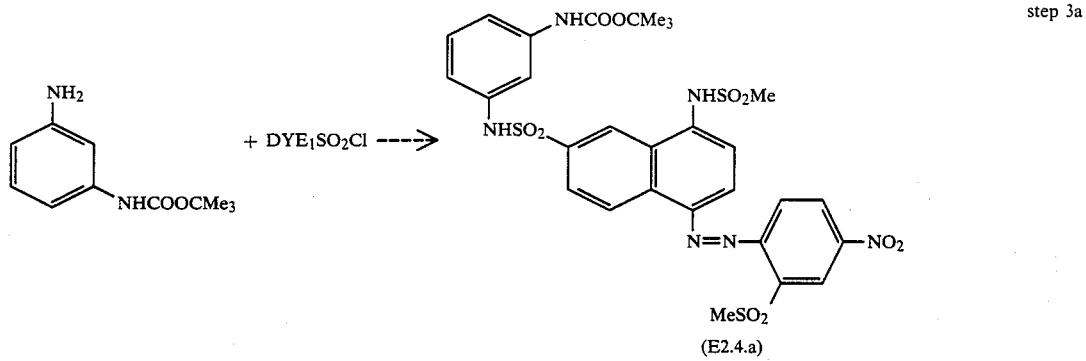

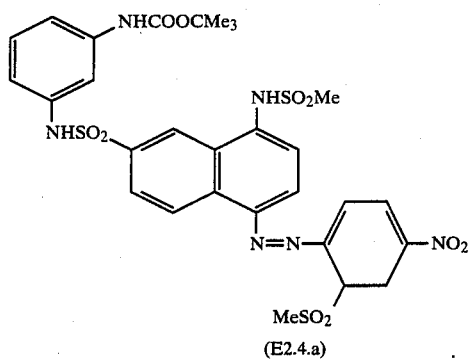 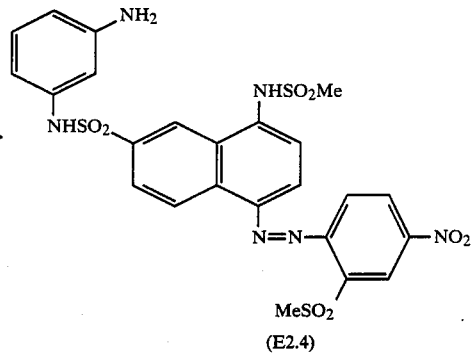

(E2.4.a) → (E2.4) step 3b

Step 1 (described in U.S. Pat. No. 4,537,853)

In a 10 l reaction flask 786 g of compound E2.1 (of which the synthesis is described in U.S. Pat. No. 4,477,554) together with 375 ml of triethylphosphite and 2 l of toluene were introduced and heated to reflux while stirring. Toluene and the during the reaction formed ethanol were distilled off till the temperature of the reaction mixture was 150° C. The mixture was kept for 1 h at 150° C. and then cooled downed to 80° C. Thereupon 6 l of n-hexane were added, the crystallized product was filtered off and washed with n-hexane and purified by recrystallization from 5 l of n-hexane. Yield: 615 g of compound E2.2.

Step 2

50 g of compound E2.2 (83.6 mmole) were added to 850 ml of ethanol. 850 ml 0.1N sodium hydroxide (1.01 eq.) was added and the mixture was stirred for about 20 minutes until all the components were dissolved. Manganese dioxide (5×5 g) was added in small portions in a period of 15 minutes while under ultrasone. The mixture was stirred for 2 h at room temperature and then extracted with 1.5 l of ethyl acetate and 400 ml of 0.5N hydrogen chloride, washed with water and dried on sodium sulfate. Yield of the crude product: 51.5 g (97%). The reaction product was recrystallized from 180 ml of hexane. Yield of the purified compound E2.3: 34.85 g (66%).

Step 3a

To a solution of m-t.butyloxycarbonylamino aniline (1.9 g, 9.1 mmole) in acetone (50 ml) and pyridine (3.7 ml) 1 eq. of solid $DYE_1SO_2Cl$ (5 g, 9.1 mmole) was added at 25° C. The solution was stirred for 3 hours and afterwards diluted with ethyl acetate (250 ml), washed with 1N hydrogen chloride (2×150 ml), water (1×150 ml) and a saturated sodium chloride solution (1×150 ml). After drying and concentrating 6.3 g of dye compound E2.4.a was obtained. Yield: 96%.

Step 3b

Compound E.2.4.a (6.3 g, 8.7 mmole) was dissolved in dry acetonitrile (75 ml). p-Toluene sulfonic acid (15 g) was added and the solution was refluxed for 15 minutes. After cooling down ethyl acetate (400 ml) was added and the mixture was washed with water (2×250 ml), a diluted sodium hydrogen carbonate solution (1×250 ml), water (2×250 ml) and a saturated sodium chloride solution. After drying and concentrating 4.8 g (89%) of compound E2.4 was obtained.

Step 3 (reference: J. Am. Chem. Soc., Vol. 79, 1957, pages 3575-3579)

To a solution of compound E2.3 (1 g, 1.63 mmole), compound E2.4 (1 g, 1.62 mmole) and N,N-dimethylaminopyridine (0.02 g) in dry dichloromethane (10 ml) at 25° C. N,N'-dicyclohexylcarbodiimide (0.334 g, 1.62 mmole) was added. The solution was stirred for 1 hour at 25° C. After filtration ethyl acetate (50 ml) was added and the solution was washed with 1N hydrogen chloride (1×15 ml) and a saturated sodium chloride solution (2×20 ml). After drying on sodium sulfate, filtration and concentration the residue was purified by column chromatography using as an eluent dichloromethane/ethanol 80:20.

The compounds according to the present invention need not necessarily be present in a photosensitive material. They may likewise be incorporated in a separate material that is used in association with a light-sensitive material e.g. an image-receiving material for use in a silver complex diffusion transfer reversal process or in a dye diffusion transfer process.

A photographic material as used herein is therefore understood to refer to light-sensitive as well as non-light-sensitive materials, generally image-recording materials.

The compounds for use according to the invention are incorporated in the coating liquid for the layers of a photographic material by one of the usual methods. The incorporation may proceed from a dispersion prepared in a sand-mill or by using ultrasound. It may be desired to incorporate the compounds according to the invention in a hydrophilic colloid layer in the form of so-called micro-capsules together with silver halide and optionally also developer substances.

The concentration of said compound capable of releasing a PUG by a nucleophilic displacement reaction may be varied over a wide range, depending upon the particular compound employed and the results which are desired; the most suitable concentration can be found with the aid of simple tests.

A light-sensitive material according to the present invention comprises in its simplest form a support carrying at least one alkali-permeable silver halide hydrophilic colloid emulsion layer which contains in operative contact therewith or therein said compound according to general formula (I), said compound being capable of releasing said photographically useful group during photographic processing.

The photosensitive silver halide may comprise silver chloride, silver bromide, silver bromoidide, silver chlorobromoiodide and the like, or mixtures thereof.

The silver halide emulsions useful in our invention are well-known to those skilled in the art. More details about their composition, preparation, shape and coating are described, e.g. in Product Licensing Index, Vol. 92, December 1971, publication 9232, pages 107 to 109.

The silver halide used in the present invention may be chemically sensitized with a chemical sensitizing agent such as compounds of sulfur, selenium or tellurium, etc., or compounds of gold, platinum, rhodium or iridium, etc., a reducing agent such as tin halide, etc., or a combination thereof. The silver halide used in the present invention can also be spectrally sensitized with methine dyes or other dyes. The emulsion may further comprise any of the well-known emulsion stabilizing and antifogging agents, coating aids, hardeners, etc. Details are described in "The Theory of the Photographic Process", T. H. James, Fourth Edition, Chapter 5, pages 149 to 169, Chapter 8, pages 194 to 234, Chapter 10, pages 251 to 290, pages 396 to 399.

Generally speaking, except when noted otherwise, the silver halide emulsion layers of light-sensitive materials comprising PUG-releasing compounds according to the present invention, comprise photosensitive silver halide dispersed, together with the said compounds, in gelatin or another aqueous alkaline solution-permeable polymeric binder. The silver halide emulsions and the compounds capable of releasing the desired PUG's may also be coated in separate layers. The location of such layers will depend upon the nature of the PUG to be released and its desired location, at the time of release, in the photographic element.

The support for the photographic elements of this invention may be any material as long as it does not deleteriously affect the photographic properties of the photographic elements. Typical flexible sheet materials are paper supports, e.g. coated at one or both sides with an α-olefin polymer e.g. polyethylene; they include cellulose nitrate film, cellulose acetate film, poly(vinyl acetal) film, polystyrene film, poly(ethylene terephthalate) film, polycarbonate film and related films or resinous materials. The support is usually about 0.05 to 0.15 mm thick. Film supports are preferably coated with at least one subbing layer to improve the adherence thereto of hydrophilic colloid layers e.g. of silver halide emulsion layers.

The photographic element may comprise layers other than the image-receiving or light-sensitive layers, for example, an antistatic layer, a protective layer, an intermediate layer, an antihalation layer, etc.

According to a special embodiment the PUG is released in the photographic material when applying an alkaline processing composition, e.g. development composition, to an imagewise exposed photographic material comprising a support carrying at least one silver halide emulsion layer and at least one alkali-permeable layer (which may be the same layer as the one containing the silver halide) comprising said compound.

An alkaline processing composition employed in this invention can be a conventional development solution comprising an alkaline material, e.g. alkali metal hydroxides or carbonates such as sodium hydroxide, sodium carbonate or an amine such as diethylamine and preferably having a pH-value higher than 11. The alkaline material can also be released from a base precursor by heating, for example, a base precursor according to the present invention.

IHR-compounds of the invention according to the present general formulae (II) and (III) have particular application in a diffusion transfer process. Photographic diffusion transfer processes have been known for several years and are summarized e.g. in "Imaging Systems" by K.I. Jacobson and R.E. Jacobson, 1977, The Focal Press and by C. C. Van de Sande in Angewandte Chemie International Edition in English, Vol. 22(3), 1983, pages 191 to 209.

Photographic image-transfer processes are based upon image formation in a photosensitive image-recording layer and diffusion in an imagewise pattern of a least one substance out of said layer to form an image in an adjacent image-receiving layer and/or to leave an imagewise distributed substance in the recording layer. The residual image in the photosensitive element is called "retained image".

In diffusion transfer color processes a dye-providing substance is associated with a silver halide emulsion. The colored image is produced by conversion of the initially non-diffusible dye-providing substance into a diffusible form or a diffusible product as a result of a silver halide development related chemical reaction. The mobilized dyes or dye precursors thus produced diffuse into a receiving layer where the final colored image is obtained.

IHR-compounds according to the invention are capable of reacting with reducing compounds, e.g. by direct or indirect reaction with non-oxidized photographic developer which remains at the non-exposed areas of negative working silver halide emulsions. By reduction a hydrolyzable substance is obtained wherefrom a diffusion-mobile part being or including a PUG e.g. dye or dye precursor is set free in alkaline medium which is capable to diffuse into an image-receiving layer where it is fixed.

In a preferred embodiment the IHR-compounds are used in conjunction with an electron-donor compound (ED-compound) or electron-donor precursor compound (EDP-compound) which yield the electrons necessary for the PUG-releasing reaction. In order to have a better control on the desired sequence of reactions the ED- or EDP-compounds are used preferably in admixture with so-called electron-transfer agents (ETA-compounds). Generally, the electron-transfer agent is a compound that is a better silver halide reduction agent under the applied conditions of processing than the electron-donor and, in those instances where the electron-donor is incapable of, or substantially ineffective in developing the silver halide, the ETA-compound functions to develop the silver halide and provides a corresponding pattern of oxidized electron-donor because the oxidized ETA-compound readily accepts electrons from the ED-compound.

The ED-compound is used preferably in non-diffusing state in each silver halide emulsion layer containing an IHR-compound. The ETA-compound on the contrary is preferably used as developing agent in diffusible state. In this way the reactions are better separated in their desired sequence in that first the imagewise oxidation of the ETA-compound by the exposed silver halide starts, then the rapid electron transfer to oxidized ETA-compound from the ED-compound takes place, which ED-compound where unaffected finally reduces the IHR-compound to make it hydrolyzable and releasing the PUG in diffusible state.

Examples of suitable ED- and ETA-compounds are given in European Pat. No. 4399 and U.S. Pat. No. 4,477,554.

In an embodiment for producing multicolor images this invention relates to photographic materials that comprise a support carrying (1) a red-sensitive silver halide emulsion layer having operatively associated therewith a compound according to one of the general formulae (II) and (III) that is initially immobile in an alkali-permeable colloid medium and wherefrom through the reducing action of silver halide developing agent and alkalinity a cyan dye is split off in diffusible state, (2) a green-sensitive silver halide emulsion layer having operatively associated therewith a compound of the type described for (1) with the difference that a magenta dye is split off in diffusible state, and (3) a blue-sensitive silver halide emulsion layer having operatively associated therewith a compound of the type described for (1) with the difference that a yellow dye is split off in diffusible state.

In a particular embodiment said IHR-compound is present in a hydrophilic colloid layer adjacent to a silver halide emulsion layer, this adjacent layer being preferably situated behind, viewed in the direction of incident light during exposure, the silver halide emulsion layer.

In a specific embodiment in accordance with this invention a photographic material being a film unit is provided that is adapted to be processed by passing said unit between a pair of juxtaposed pressure-applying members, such as would be found in a camera designed for in-camera processing. The unit comprises (1) a photosensitive element, which contains a silver halide emulsion layer having associated therewith a said IHR-compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit such as a rupturable container, which is adapted to be positioned during processing of the film so that a compressive force applied to the container by the pressure-applying members will effect a discharge of the container's contents within the film, and (4) a silver halide developing agent, which is soluble in the alkaline processing composition located within said film unit.

For in-camera processing the photosensitive material is preferably composed such that the photosensitive silver halide emulsion layer(s) is (are) negative-working and applied to the same support as the receptor layer so as to form an integral combination of light-sensitive layer(s) and a non-light-sensitive layer receiver element preferably with an opaque layer, which is alkali-permeable, reflective to light and located between the receptor layer and the silver halide emulsion layer(s). In a process using such material the alkaline processing composition may be applied between the outer photosensitive layer of the photographic element and a cover sheet, which may be transparent and superposed before exposure.

In a photographic element according to the invention and containing two or more silver halide emulsion layers, each silver halide emulsion layer containing a dye image-providing material or having the dye image-providing material present in a contiguous layer may be separated from the other silver halide emulsion layer(s) in the film unit by (an) interlayer(s), including e.g. gelatin.

According to an embodiment in the preparation of a multicolor diffusion transfer material according to the present invention, a water-permeable colloid interlayer dyed with a yellow non-diffusing dye or Carey Lea silver is applied below the blue-sensitive silver halide emulsion layer containing a yellow dye-releasing compound.

In certain embodiments of the invention and especially with integral format film units, an opacifying agent can be applied from a processing composition. Examples are given in European Pat. No. 4399 and U.S. Pat. No. 4,477,554.

For use in color photography any material can be employed as the image-receiving layer as long as the desired function of mordanting or otherwise fixing the diffused dye will be obtained. The particular material chosen will, of course, depend upon the dye to be mordanted. In the image-receiving layer a pH-lowering material can be used to increase the stability of the transferred image. An inert timing or spacing layer may be employed over the pH-lowering layer, which times or controls the pH reduction depending on the rate at which alkali diffuses through the inert spacer layer. Examples of the composition of suitable image-receiving layers are given in European Pat. No. 4399 and U.S. Pat. No. 4,477,554.

According to another embodiment the PUG is released in the photographic material when applying heat.

For example, a base precursor of the present invention can be employed in thermally developable light-sensitive silver halide materials and in processes using them, as described in, for example, "Neblette's Handbook of Photography and Reprography", Seventh Edition (Van Nostrand Reinhold Company), 1977, pages 32 and 33, U.S. Pat. Nos. 3,152,904, 3,301,678, 3,392,020 and 3,457,075, Great Britian Pat. No. 1,131,108 and Research Disclosure (June 1978) item 17029.

These latter processes comprise the step of heating the imagewise exposed photographic material comprising a support carrying a layer containing a silver halide emulsion, a developing agent for silver halide and a base precursor, in a substantially water free state (a state which is in equilibrium with water in the air but water is not fed from the outside of the system), during which step alkaline materials, which activate development, are released from the base precursor.

The term "base precursor" herein used means a substance which releases a basic component by thermal decomposition, i.e., compounds which are stable at ordinary temperature and, when heated to temperatures higher than a certain temperature, rapidly release a basic substance. The released base is an organic base preferably a base with a pKa value of about 9 or higher and a boiling point of about 100° C. or higher, in particular a base with a pKa value of 10 or higher, for example guanidine, cyclic guanidine, amidine and cyclic amidine.

Conventional base precursors are the salts of carboxylic acids and organic bases. Examples of suitable carboxylic acids include trichloroacetic acid, trifluoroacetic acid, etc., and examples of suitable bases include guanidine, piperidine, morpholine, p-toluidine, 2-picoline, etc. A characteristic of these latter base precursors is the fact that the carboxyl group undergoes a decarboxylation; when heated $CO_2$ is released with the adverse effect of gas bubbles being formed in the photographic material wherein the base precursors are incorporated. The base precursors of the present invention do not have the above discussed defects.

The base precursors of the present invention can be used in an amount over a wide range. It is preferred to use them in an amount of 50% by weight or less based on the total weight of the coating layer. More preferably, a range of 0.01% by weight to 40% by weight is suitable. The base precursors of the present invention may be used alone, or two or more of them may be used in combination, if desired.

In the thermally developable photographic material the use of a water-releasing compound is advantageous. A water-releasing compound is a compound which is decomposed during the heat development to release water. In particular anorganic salts containing crystal water e.g. $NaSO_4.10H_2O$, $NH_4Fe(SO_4)_2.12H_2O$ can be used.

The photothermographic process can be performed in the presence of a heat solvent. By the term "heat solvent" is meant a non-hydrolyzable organic material which is in a solid state at the environmental temperature but melts at a temperature of heat treatment (thus creating a fluid medium in which the development proceeds faster) or melts at a lower temperature of heat treatment when present with other components.

The heat-developable photographic material used in the present invention may contain, if necessary, various additives known as additives for heat-developable photographic materials including those additives described in item 17029, Research Disclosure (June 1978).

In this invention, the latent image obtained on the photothermographic material by light exposure, can be developed by overall heating the light-sensitive material to a temperature of about 80° C. to about 250° C. for about 0.5 seconds to about 300 seconds. The heating temperature may be desirably selected in the foregoing temperature range with the increase or decrease of the heating time. In particular, a temperature range of about 110° C. to about 160° C. is useful. The heating means may be a simple hot plate, a hot iron, a hot roller, an exothermic material utilizing carbon, etc., or similar materials. The heating may also be conducted at the same time with the exposure.

The present invention will now be described in greater detail by reference to the following examples which are given here for illustrative purposes only and are by no means intended to limit the scope of the invention.

EXAMPLE 1: Thermal release of base

The releasing of a basic component by the aforesaid base precursors upon heating can be ascertained by various methods. For example, such analytical means as gas chromatography may be used.

The cyclization reaction was carried out while coupled to a gas chromatograph - mass spectrometer. Three aspects of the cyclization reaction were studied in this way: (1) identification of the released base, (2) identification of the cyclic residue, (3) base release as a function of temperature by means of a thermal desorption cold trap injector (TCT).

The TCT-procedure comprises the steps of heating a solution of a base precursor according to the present invention for 5 minutes at different temperatures and after partial base release further heating the solution to a higher temperature till all the base is released. The temperatures used were 70° C., 90° C., 110° C. and 130° C.

The gas chromatographic identification of the released material was based on the pure base as a reference.

All the tested base precursors according to the present invention cyclize and release the corresponding base at temperatures between 90° C. and 130° C. (table 2).

TABLE 2

| T | area under the peak of the released base in % (largest for each compound = 100%) | | | | | | |
|---|----|----|-----|-----|-----|-----|-----|
|   | A1 | A7 | A13 | A19 | A31 | A61 | A85 |
| 70° C. | 8 | 9 | | 1 | | | |
| 90° C. | 26 | 61 | 72 | 37 | 44 | 12 | |
| 110° C. | 48 | 100 | 100 | 93 | 65 | 60 | 17 |
| 130° C. | 100 | 97 | 81 | 100 | 100 | 100 | 81 |

Mass spectrometric analysis of the obtained residue revealed that the reaction product is almost exclusively the cyclic form (IV).

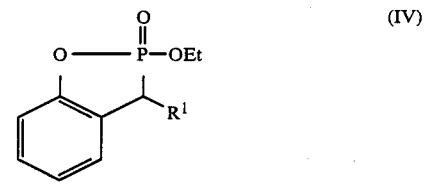

A1 m/z = 198
A7 m/z = 212

Another very simple method to ascertain the release of a base is the following.

1 ml of distilled water was added to 100 mg (0.253 mmole) of compound A18 and the pH measured: pH=7. When the same amount of compound was first fused and kept at 180° C. for 3 minutes the pH of the aqueous solution was 11.

When 100 mg of compound A13 was kept at 120° C. for 2 minutes and then diluted with 0.5 ml of distilled water the pH was 11.

EXAMPLE 2: Photographic material (1) A subbed polyethylene terephthalate support coated with a layer containing gelatin (3 g/m²), AgCl expressed as $AgNO_3$ (1 g/m²) and compound B10 (1 g/m²).

(2) Idem as (1) containing the compound B10 in a dispersion with dibutylphthalate 1/1.

(3) Idem as (2) containing also 0.95 g/m² of the cyan coupler 1-hydroxy-4-chloro-2-hexadecylnaphthamide.

The obtained photographic materials were exposed through a grey wedge and processed for 1 minutes with a 2% sodium carbonate solution in water at 40° C., rinsed for 10 secondes, bleach-fixed for 1 minute in Agfa-Gevaert's G470 and rinsed for 5 minutes. A negative cyan wedge was obtained in all three photographic materials. The visual light spectral density was measured with a MACBETH (trade name) densitometer RD-919 in the Status A mode and yielded for material (1) 0.57, for material (2) 0.85 and for material (3) 0.86. This experiment proves that the p-phenylenediamine compound is released from compound B10 and that the released developer after oxidation couples with the remaining phenolic residue or with the added naphthol coupler to an azomethine dye.

The photographic materials were exposed as described above, processed with a 2% sodium carbonate solution at 40° C. for 1 minute, rinsed for 5 minutes and dried. Negative cyan wedges with silver images were obtained in the three photographic materials. The three wedges were contacted with a COPYCOLOR CCP receptor material in a COPYPROOF CP 38 diffusion transfer processing apparatus having in its tray a COPYCOLOR CC 292 solution (COPYPROOF and COPYCOLOR are tradenames of Agfa-Gevaert N.V., Belgium). Only the CCP material is wetted in the apparatus. After a contact time of 1 minute the receptor material and the light-sensitive material were peeled apart, rinsed and dried. Brilliant cyan wedges with the following densities were obtained: for material (1) 0.76, for material (2) 1.25 and for material (3) 0.93. The residual silver images were bleach-fixed and rinsed. The strips (1) and (2) contained almost no cyan dye image anymore while strip (3) still contained a cyan image with a maximum density of 0.99. This experiment demonstrates that p-phenylenediamine is released, that the released developing agent after oxidation can couple with the residual phenolic compound to a non-diffusion resistant azomethine dye and with the diffusion resistant naphthol coupler and that the ratio between the two coupling rates is approximately 1:1.

I claim:

1. A photographic material comprising a support carrying at least one alkali-permeable hydrophilic colloid layer containing an intramolecular nucleophilic displacement compound or a precursor thereof wherefrom during photographic processing a photographically useful group can be split off, said intramolecular nucleophilic displacement compound or precursor thereof corresponding to the following general structure (I):

wherein
$Nu^1$ represents a nucleophilic group or precursor thereof being located in adjacent position to $C(R^1R^2)$ so as to make possible elimination of PUG through a nucleophilic displacement reaction;
Ar represents an aryl group or a heteroaryl group, which groups may be substituted by one or more mono-atomic or poly-atomic groups or by substituents which, when in adjacent positions on the ring, together form a ring fused with the (hetero)aryl group;
each of $R^1$ and $R^2$ (same or different) represents hydrogen or an alkyl, an aryl or an aralkyl group;
$R^3$ represents an alkyl, an aralkyl, an alkyloxy, an aryloxy, an alkylthio, an arylthio, an amino group, an oxy ($O^-$) or a hydroxy group;
PUG is a group containing a hetero atom (selected from among N, S and O) through which it is attached to the phosphor atom and producing a photographically useful activity after cleavage of the bond between the hetero atom and the phosphor atom.

2. A photographic material according to claim 1 wherein the nucleophilic group $Nu^1$ is an HO group or an RO group wherein R is an alkyl, an acyl, an aryl or a trialkylsilanyl group.

3. A photographic material according to claim 1 wherein Ar is substituted by an alkyl group, a nitro group, a cyano group, a carboxy group, substituents which, when in adjacent positions on the ring, together form a ring fused with Ar or by another nucleophilic group $Nu^2$ (same as or different from $Nu^1$).

4. A photographic material according to claim 1 wherein in at least one of the substituents $R^1$, $R^2$ and $R^3$ or in a substituent of Ar a ballasting group is present to render said compound immobile in the alkali-permeable layer of the photographic material.

5. A photographic material according to claim 1 wherein the photographically useful group PUG after release represents a base or a fogging agent or a silver halide developing agent or a precursor of a silver halide developing agent.

6. A photographic material according to claim 1 wherein the photographically useful group PUG after release represents a p-phenylenediamine compound.

7. A photographic material according to claim 1 wherein the intramolecular nucleophilic displacement compound corresponds to one of the following general formulae (II) and (III):

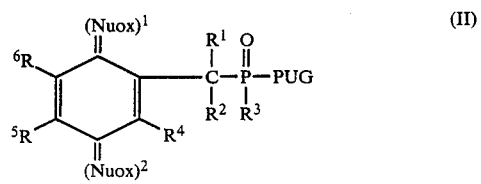

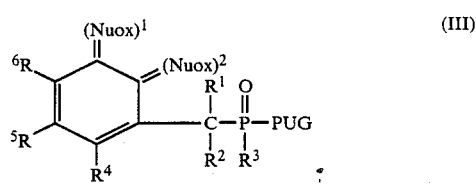

wherein:
each of $(Nuox)^1$ and $(Nuox)^2$ (same or different) represents an oxidized nucleophilic group;
each of $R^1$ and $R^2$ (same or different) represents hydrogen or an alkyl, an aryl or an aralkyl group;
$R^3$ represents an alkyl, an aralkyl, an alkyloxy, an aryloxy, an alkylthio, an arylthio, an amino group, an oxy ($O^-$) or a hydroxy group;
each of $R^4$, $R^5$ and $R^6$ represents a mono-atomic group or a poly-atomic group or $R^4$ and $R^5$ together when in adjacent positions on the ring form a ring fused with the remainder of the molecule or $R^5$ and $R^6$ together form a ring fused with the remainder of the molecule;
PUG is a group containing a hetero atom (selected from among N, S and O) through which it is attached to the phosphor atom and producing a photographically useful activity after cleavage of the bond between the hetero atom and the phosphor atom.

8. A photographic material according to claim 7 wherein each of $R^4$, $R^5$ and $R^6$ represents hydrogen, a halogen atom, an alkyl group, an aryl group, an alkyloxy group, an alkylthio group or an acylamino group wherein the acyl group is derived from aliphatic or aromatic carboxylic or sulfonic acids.

9. A photographic material according to claim 7 wherein in at least one of the substituents $R^1$, $R^2$, $R^3$, $R^4$, $R^5$ and $R^6$ a ballasting group is present to render said compound immobile in the alkali-permeable layer of the photographic material.

10. A photographic material according to claim 7 wherein the photographically useful group PUG represents a group X-DYE wherein DYE represents a dye and X represents

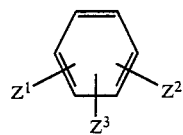

wherein:

each of $Z^1$ and $Z^2$ (same or different) represents a linking O, NH, $SO_2$, $SO_3$, CO, $CO_2$ or $NHSO_2$;

$Z^3$ represents hydrogen, $SO_3H$, $CO_2H$ or NHMe.

11. A photographic material according to claim 7 wherein the group $(Nuox)^1$ and the group $(Nuox)^2$ are each O groups.

12. A photographic material according to claim 1 wherein said alkali-permeable layer is a light-sensitive silver halide emulsion layer.

13. A photographic material according to claim 12 wherein the photographic material contains in a light-sensitive silver halide emulsion layer a color coupler compound and wherein the photographically useful group PUG after release from the intramolecular nucleophilic displacement compound represents a p-phenylenediamine compound which after oxidation can couple with the coupler compound.

* * * * *